United States Patent
Hansen et al.

(10) Patent No.: US 12,038,359 B2
(45) Date of Patent: Jul. 16, 2024

(54) METHOD FOR DIRECT INOCULATION OF A BROTH FROM A SOURCE SUSPENSION

(71) Applicant: BD KIESTRA B.V., Drachten (NL)

(72) Inventors: Timothy Roy Hansen, Spring Grove, PA (US); Martijn Kleefstra, Surhuisterveen (NL); Michael Bois, Brooklyn, NY (US); Timothy M. Wiles, Ocean Isle Beach, NC (US); Charles Chak Cheung Yu, Lutherville, MD (US)

(73) Assignee: BD KIESTRA B. V., Drachten (NL)

( * ) Notice: Subject to any disclaimer, the term of this patent is extended or adjusted under 35 U.S.C. 154(b) by 500 days.

(21) Appl. No.: 17/255,299

(22) PCT Filed: Jun. 24, 2019

(86) PCT No.: PCT/US2019/038644
§ 371 (c)(1),
(2) Date: Dec. 22, 2020

(87) PCT Pub. No.: WO2020/005792
PCT Pub. Date: Jan. 2, 2020

(65) Prior Publication Data
US 2021/0199546 A1 Jul. 1, 2021

Related U.S. Application Data

(60) Provisional application No. 62/689,419, filed on Jun. 25, 2018.

(51) Int. Cl.
*G01N 1/38* (2006.01)
*C12Q 1/18* (2006.01)
(Continued)

(52) U.S. Cl.
CPC ............... *G01N 1/38* (2013.01); *C12Q 1/18* (2013.01); *C12Q 1/24* (2013.01); *G01N 1/40* (2013.01); *G01N 2001/386* (2013.01)

(58) Field of Classification Search
CPC ...... G01N 1/38; G01N 1/40; G01N 2001/386; C12Q 1/18; C12Q 1/24
See application file for complete search history.

(56) References Cited

U.S. PATENT DOCUMENTS
2008/0072664 A1    3/2008   Hansen et al.

FOREIGN PATENT DOCUMENTS
CN    1708511 A    12/2005
CN    206975048 U   2/2018
(Continued)

OTHER PUBLICATIONS

PCT International Search Report and Written Opinion issued in corresponding PCT application No. PCT/US2019/038644 on Sep. 26, 2019.
(Continued)

*Primary Examiner* — Jill A Warden
*Assistant Examiner* — Alex Ramirez
(74) *Attorney, Agent, or Firm* — Botos Churchill IP Law LLP

(57) ABSTRACT

An automated method for preparing a sample suspension. The sample suspension can be used for both MALDI and antimicrobial susceptibility (AST). A suspension is prepared, and a portion of that suspension is removed for a first analysis (e.g. MALDI), leaving a remaining volume. The turbidity of the remaining volume is measured. If the turbidity is below a first threshold, the suspension is not used for a second analysis (e.g. AST) and is subjected to a concentration protocol to raise the turbidity of the suspension. If the turbidity is within a predetermined range, a (Continued)

volume of the suspension is calculated that will deliver a predetermined amount of sample to a vessel for the second analysis. If the turbidity of the suspension is above the predetermined range, and the suspension has not been diluted a predetermined number of times, the suspension is diluted according to a dilution protocol.

13 Claims, 8 Drawing Sheets

(51) Int. Cl.
*C12Q 1/24* (2006.01)
*G01N 1/40* (2006.01)

(56) References Cited

FOREIGN PATENT DOCUMENTS

| JP | 2010213598 | A | | 9/2010 | |
|---|---|---|---|---|---|
| RU | 2639777 | C2 | | 12/2017 | |
| WO | 2004039835 | A2 | | 5/2004 | |
| WO | 2016034554 | A1 | | 3/2016 | |
| WO | 2016051267 | A2 | | 4/2016 | |
| WO | 2016191646 | A2 | | 12/2016 | |
| WO | WO-2016191646 | A2 | * | 12/2016 | ............ C12M 33/04 |

OTHER PUBLICATIONS

Office Action from corresponding Indian Application No. 202117000879 dated Dec. 8, 2022 (6 pp.).
Office Action from corresponding Russian Application No. 2021101225 dated Oct. 27, 2022 (7 pp.).
Konishi, et al., Captures Cell Growth—From Measuring Method to Specific Velocity Calculation—Biotechnology, 2015, vol. 93, No. 3, pp. 149 to 152 (9 pp.).
Office Action from corresponding Japanese Patent Application No. 2020-573532 dated Jun. 13, 2023 (6 pp.).
Decision to Grant issued in corresponding Russian Patent Application No. 2021101225/10 dated Sep. 13, 2023 (21 pp.).
Decision of Rejection issued in corresponding Japanese Patent Application No. 2020-573532 on Oct. 26, 2023 (12 pp.).
CN Search Report issued in corresponding CN application No. 2019800522464 on Dec. 1, 2023, pp. 3.
Chinese First Office Action issued in corresponding CN application No. 201980052246.4 on Dec. 1, 2023, pp. 9.
Yang, Han, et al., Ultrasonic dispersion ratio turbidimetry treatment BACTEC MGIT 960fosterValue of positive bacterial specimens for drug susceptibility testing, China issue magazine 2019 year, 41 Volume, Jul. 2019,vol. 41, No. 7.743., pp. 9.
Article 94 Communication issued in Corresponding EP application No. 19737403.6 on Dec. 12, 2023.

* cited by examiner

| DrugCode | MICValue | MIC | AntimicrobialSIRResult | AntimicrobialFinalSIRResult |
|---|---|---|---|---|
| AMC | 8 | <=8/4 | S | S |
| AN | 8 | <=8 | S | S |
| ATM | 2 | <=2 | S | S |
| C | 4 | <=4 | S | X |
| CAZ | 1 | <=1 | S | S |
| CIP | 0.5 | <=0.5 | S | S |
| CL | 1 | <=1 | | |
| CRO | 1 | <=1 | S | S |
| CXM | 4 | <=4 | S | S |
| CZ | 2 | <=2 | S | X |
| ETP | 0.25 | <=0.25 | S | S |
| FEP | 1 | <=1 | S | S |
| FF | 16 | <=16 | S | S |
| FM | 16 | <=16 | S | S |
| FOX | 4 | <=4 | S | S |
| GM | 2 | <=2 | S | S |
| IPM | 0.25 | <=0.25 | S | S |
| LVX | 1 | <=1 | S | S |
| MEM | 0.125 | <=0.125 | S | S |
| MI | 1 | <=1 | S | S |
| MXF | 0.5 | <=0.5 | S | S |
| NN | 2 | <=2 | S | S |
| NOR | 2 | <=2 | S | S |
| SAM | 4 | <=4/2 | S | S |
| SCP | 0.5 | <=0.5/8 | | |
| SXT | 1 | <=1/19 | S | S |
| TE | 2 | <=2 | S | S |
| TGC | 1 | <=1 | S | S |
| TZP | 4 | <=4/4 | S | S |

FIG.6

METHOD FOR DIRECT INOCULATION OF A BROTH FROM A SOURCE SUSPENSION

CROSS-REFERENCE TO RELATED APPLICATIONS

The present application is a national phase entry under 35 U.S.C. § 371 of International Application No. PCT/US2019/038644, filed Jun. 24, 2019 published in English, which claims priority from U.S. Provisional Application Ser. No. 62/689,419, filed Jun. 25, 2018, all of which are incorporated herein by reference.

BACKGROUND OF THE INVENTION

Disclosed herein is a method for using a single suspension for both the identification and antimicrobial susceptibility of microorganisms in a biological sample (e.g. blood).

As a routine practice in medical diagnosis, biological samples such as blood are extracted from patients and analyzed. Depending upon indications, the samples may be analyzed to determine if microorganisms are present in the sample, e.g., by blood culture (such as the BACTEC™ FX and BACTEC™ 9000 series from Becton, Dickinson and Company) or by streaking onto an agar plate (manually or by an automated instrument such as the Innova™ or Inoqula sold by Becton, Dickinson and Company). If microorganisms are determined to be present, there is both medical and economic justification to both identify the specific microorganism present and, to facilitate treatment, the antibiotic resistance/susceptibility of the microorganism.

Many kinds of microorganism (which will also be referred to below as microbes), particularly bacteria and unicellular fungi, can be identified by mass spectrometric ("mass spec") processes, such as Matrix Assisted Laser Desorption Ionization ("MALDI"). In the MALDI process, small quantities of microbes from a colony cultivated in the usual way in a nutrient medium are transferred to a mass spectrometric sample support plate known as a MALDI plate, and then subjected directly to mass spectrometric analysis, generally by MALDI time-of-flight (TOF). The mass spectrometry analysis shows the different proteins, provided they are present in the microbes in sufficient concentration. The identity of the microbe is then determined from the microbe's protein profile through a computerized search of spectral libraries containing thousands of reference spectra. If no reference mass spectrum is present in a library for the precise species of microbe being examined, computerized library searches with looser similarity requirements can provide at least some indication of the order, family or genus of the microbes, since related microbes frequently contain a number of identical protein types. The MALDI process is described in further detail in International Publication No. WO-2009/065580A1 to Ulrich Weller entitled "Identification of Pathogens in Bodily Fluids," the content of which is hereby incorporated in its entirety. A variety of mass spectrometry instruments may be used for identification.

It is desirable to analyze the effectiveness of an antimicrobial agent in inhibiting the growth of microbial isolates from clinical specimens. Such analysis is known as antimicrobial susceptibility testing ("AST"). An AST technique of the background art is a dilution technique which involves exposing bacteria to decreasing concentrations of antimicrobial agents in liquid media by serial two-fold dilution. The lowest concentration of an antimicrobial agent in which no visible bacterial growth occurs is defined as the minimal inhibitory concentration ("MIC"). The MIC is the standard measure of antimicrobial susceptibility. AST instruments are known in the art, such as the BD Phoenix™ system sold by Becton, Dickinson and Company, which performs both identification and AST.

An apparatus known in the background art that can prepare specimens for such AST processes is the BD Phoenix™ AP, available from Becton, Dickinson and Company. The workflow typically includes preparing an inoculum, such as by labeling the appropriate tube, selecting microbial colonies and making a heavy suspension in ID broth tubes, and placing the tubes in one or more racks holding AST broth tubes. The workflow next includes performing automated nephelometry to adjust the ID tube to a 0.5 or 0.25 McFarland ("McF"), adding AST indicator to the AST broth, transferring part of the sample to the AST broth, and mixing both tubes. The workflow next includes having the healthcare worker remove the processed ID and AST tubes and place them on an inoculation station having ID/AST Panels, such as Phoenix Panels, and inoculating the specimens in the Panels. See also U.S. Patent Application Publication No. 2008/0072664A1, the content of which is hereby incorporated in its entirety.

The Panels are then maintained within an ID/AST system (e.g., a Phoenix instrument) having a controlled environment (e.g., controlled temperature, humidity, light exposure, etc.) for a predetermined amount of time in order to promote microbial growth in the presence of the antimicrobial agent. The system typically includes an analysis capability in order to measure microbial growth in one or more microwells without disrupting the maintenance of a controlled environment. The system may also include a capability to report the analysis results to additional devices for further processing. Such system may include both ID and AST capability, or only ID or only AST capability. Moreover, even an ID/AST system can be run for only ID or only AST results. Panels See, e.g., U.S. Pat. Nos. 5,922,593, 6,096,272, 6,372,485, 7,115,384, and 6,849,422, the contents of which are hereby incorporated by reference in their entirety.

The various laboratory apparatus may be in communication with a data management system, such as the BD EpiCenter™, in order to provide a single location for a laboratory worker to monitor status and results from the various laboratory apparatus. Monitoring, analyzing and communicating microbiology data in a timely manner can directly impact patient care. However, obtaining, organizing and communicating information from the various laboratory apparatus is labor intensive. Current information systems can make even routine identification and AST testing difficult. Microbiologists, infection control officers, physicians and pharmacists need immediate access to patient-focused information to rapidly identify and react to emerging resistance or HAI events.

Methods and apparatus in which a common sample suspension is made for both MALDI and AST are described in U.S. Pat. No. 9,180,448 which issued on Nov. 10, 2015 from an application filed on Jul. 6, 2011 and entitled "Method and Apparatus for Identification of Bacteria" which is assigned to Becton, Dickinson and Company. Other systems that acquire a sample and create a suspension from the sample for both MALDI and AST are described in U.S. Pat. No. 9,556,495 which issued on Jan. 31, 2017 from U.S. patent application Ser. No. 14/388,430 filed on Apr. 2, 2013, which is assigned to BD Kiestra B.V. and is entitled "Automated Selection of Microorganisms and Identification Using MALDI." Another system is described in US2016/034554 which was filed on May 27, 2016 and is assigned to BD Kiestra B.V. The '448 Patent, the '495 Patent and the '554 Patent Publication are all incorporated by reference.

BRIEF SUMMARY OF THE INVENTION

In one embodiment, the invention described herein is an automated method in which a common sample suspension is used as a source for sample for both a system that identifies microorganisms determined to be present in the sample and a system that tests the microorganisms for their antimicrobial resistance/susceptibility. The system has a first station that prepares the common suspension for both a mass spec (e.g., MALDI) process for microorganism identification and for antimicrobial susceptibility testing (AST).

According to the method, a sample is inoculated into a diluent. In one embodiment, the sample is picked from culture plate. Picking a sample from a culture plate is known to those skilled in the art and is not described in detail herein. Picking a sample from a culture plate and depositing the sample into a diluent is described in WO/2016/034554.

The picked sample is deposited into a sample diluent. Such diluents are well known and not described in detail herein. Such diluents are described in WO/2016/034554.

The turbidity of the sample is then measured. A nephelometer is used to obtain turbidity measurements. Measuring turbidity using a nephelometer is described in WO/2016/034554. If the measured turbidity is within a predetermined range, then a first aliquot of the suspension is used for MALDI and a second aliquot of the suspension is delivered into a broth tube for antibiotic susceptibility testing (AST). The volume of suspension used for AST is calculated from the suspension turbidity, since AST requires that a certain amount of CFU (colony forming units) of sample be delivered into the AST broth tube, a volume is calculated based on suspension turbidity and target amount of inoculated sample. The predetermined turbidity range is necessary because of the limitations imposed by automatic pipetting apparatus. Broth used as a nutrient or culture media to allow microorganisms to grow in AST is well known to one skilled in the art and not described in detail herein. In AST, the absence of microbial growth indicates that the microorganism being tested is susceptible to an antibiotic delivered into combination with the sample suspension. AST broth is also referred to as culture media herein.

The amount of the suspension that is used to inoculate plates for identification (e.g. MALDI plates) or broth tubes for antibiotic susceptibility testing (AST) is based on the amount of sample carried per unit volume of suspension. Once the suspension is created, if the concentration of the sample in suspension (i.e. sample turbidity) is too high, then the volume of suspension required to inoculate that amount of sample onto the MALDI plate or into the AST broth tubes could be quite small. Small volumes are difficult to pipette accurately. Conversely, a larger volume of a very "light" suspension is required to inoculate the MALDI plate or broth tube with the target amount of sample. However, the volume that can be transferred using conventional pipettors is limited.

Consequently, if the amount of sample delivered into the suspension is such that the sample concentration in suspension (as measured by suspension turbidity) is higher than a predetermined range (e.g. about 0.2 McFarland to about 2 McFarland) then the suspension is subjected to a dilution protocol to reduce the turbidity such that the suspension turbidity is within that predetermined range. If the amount of sample delivered into suspension is such that the suspension turbidity is below the predetermined range, then the suspension is subjected to a concentration protocol. In one embodiment, the concentration protocol calls for acquiring additional sample to increase the concentration of the sample in the suspension. However, if no additional sample is available, then the concentration protocol calls for the suspension to be discarded.

The preparation of a suspension and inoculation of a MALDI plate with such a prepared suspension is described in WO/2016/034554, which is incorporated by reference herein. The MALDI process occurs at a second station and the AST occurs at a third station.

After the aliquot of the suspension has been removed for MALDI, the system determines how much of the suspension to be used to inoculate the AST panel. The volume amount of suspension is determined by the total amount of sample required by a predetermined specification to be introduced into the AST broth tube. Based on the known turbidity of the suspension and the target amount of the sample for panel inoculation, the system calculates the volume of the suspension required to inoculate the AST broth tube. The system then acquires the specified suspension volume and inoculates the panel with that volume. The system and method herein do not require that the turbidity of the suspension be adjusted to a standardized McFarland value for AST after the aliquot of sample for MALDI is removed from the suspension tube, making the method and system more efficient and less equipment-intensive than systems and methods that require standardizing the turbidity of the suspension to a target McFarland value prior to inoculation of the AST broth tube using the suspension.

The system has a user interface and software where samples are tracked so that the test results from the second and third stations are linked to the sample and the patient from whom the sample was obtained. The system also includes a station for determining if microorganisms are present in the sample and only those samples in which microorganisms are determined to be present are subjected to further processing and testing.

BRIEF DESCRIPTION OF THE DRAWINGS

FIG. 6 is a summary of the AST results using suspension prepared by the methods of FIGS. 4 and 5.

DETAILED DESCRIPTION

The disclosure herein refers to a sample preparation apparatus (sample prep or prep station hereinafter) as a "Phoenix AP", or an AST system as a BD Phoenix™ or refer to data management system with user interface as a "BD EpiCenter" system, or refer to a blood culture analysis apparatus as a "BD BACTEC™," or refer to a mass spectrometry system as MALDI, but it should be understood that the meaning of these terms is not limited to the apparatus having these trademarked names, but may include apparatus having a substantially similar functionality. Apparatus having substantially similar functionality may include the BacT/Alert (bioMerieux) and VersaTREK (Trek) blood culture systems, and the Vitek (bioMerieux) and MicroScan (Siemens Healthcare) ID/AST systems.

In one embodiment, the system described herein integrates the microbial identification capabilities of a MALDI instrument with the AST and data processing capabilities of a laboratory analysis or processing system such as the Phoenix, Phoenix AP, BACTEC, or EpiCenter systems.

In another embodiment, the Phoenix AP is modified to prepare not only the AST inoculum for the Phoenix Panels, but also prepare the same sample for the MALDI plate. This feature provides an automation benefit of positive identification for the sample prepared on the MALDI plate, by ensuring that the isolate applied to the MALDI plate is from the exact same sample used for antimicrobial susceptibility testing.

The MALDI, sample prep, AST system, and/or blood culture instruments are in communication with a data management system such as the EpiCenter system. EpiCenter provides the real-time data access and analysis tools to improve patient care. EpiCenter is able to monitor, analyze and communicate microbiology data in a timely manner, thereby directly controlling, monitoring, and improving patient care. Phoenix produces the AST result, and the MALDI instrument produces the identification result. EpiCenter combines the results, and applies expert rules to produce the final ID/AST results for the sample. An example of such a system that applies expert rules is BDXpert™.

Figure 7:
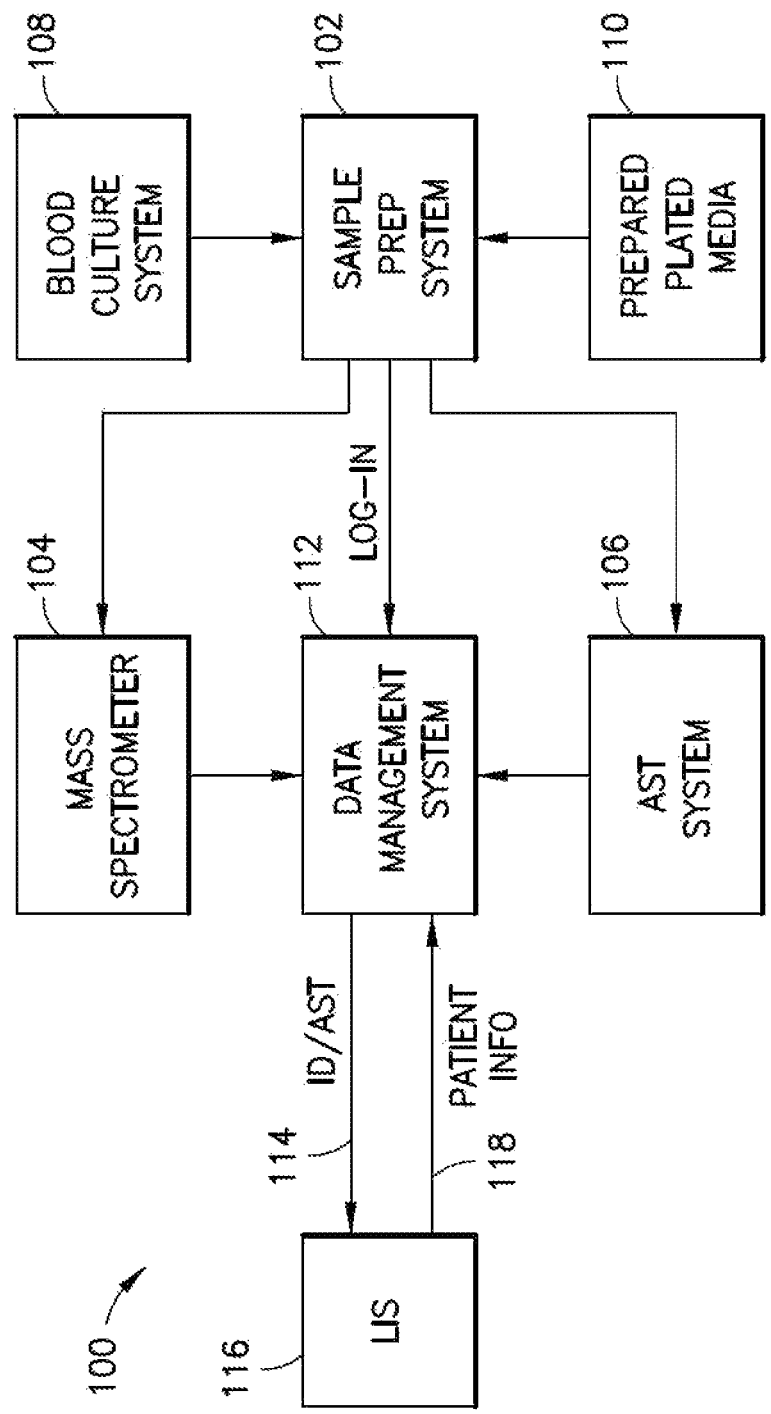
FIG. 7 is a system schematic.

FIG. 7 shows a block diagram of a system 100 that detects and analyzes microbial samples, in accordance with an embodiment of the invention. The various components of system 100 include a sample prep station 102 (such as a Phoenix AP), a mass spec instrument 104 (such as a MALDI-TOF), an AST system 106 (such as a Phoenix), a blood culture system 108 (such as a BACTEC instrument), prepared plated media 110 (e.g., manually prepared or prepared by a system such as the Innova), a data management system 112 (such as EpiCenter), and a Laboratory Information System 116 ("LIS") that receives data from the data management system 112 via ID/AST link 114, and which provides patient information to the data management system 112 via PT Info link 118.

In the system 100, the sample prep system is provided with bacteria, e.g., picked from a prepared plate or taken from a blood culture vial. In one embodiment, cuvettes are over inoculated with the bacterial sample. The cuvettes are advantageously used as the source of sample for both ID and AST. This ensures that not only the same patient sample, but also the same isolate, is subject to the ID and AST testing.

Sample prep station 102 prepares the sample, for both ID and AST, while the AST system 106 produces the AST result and the mass spec instrument 104 produces the ID result. Data management system 112 stores the ID result and AST result, optionally applying expert rules to produce the final combined ID/AST results for the sample, and also interacts with the LIS system.

Figure 1:
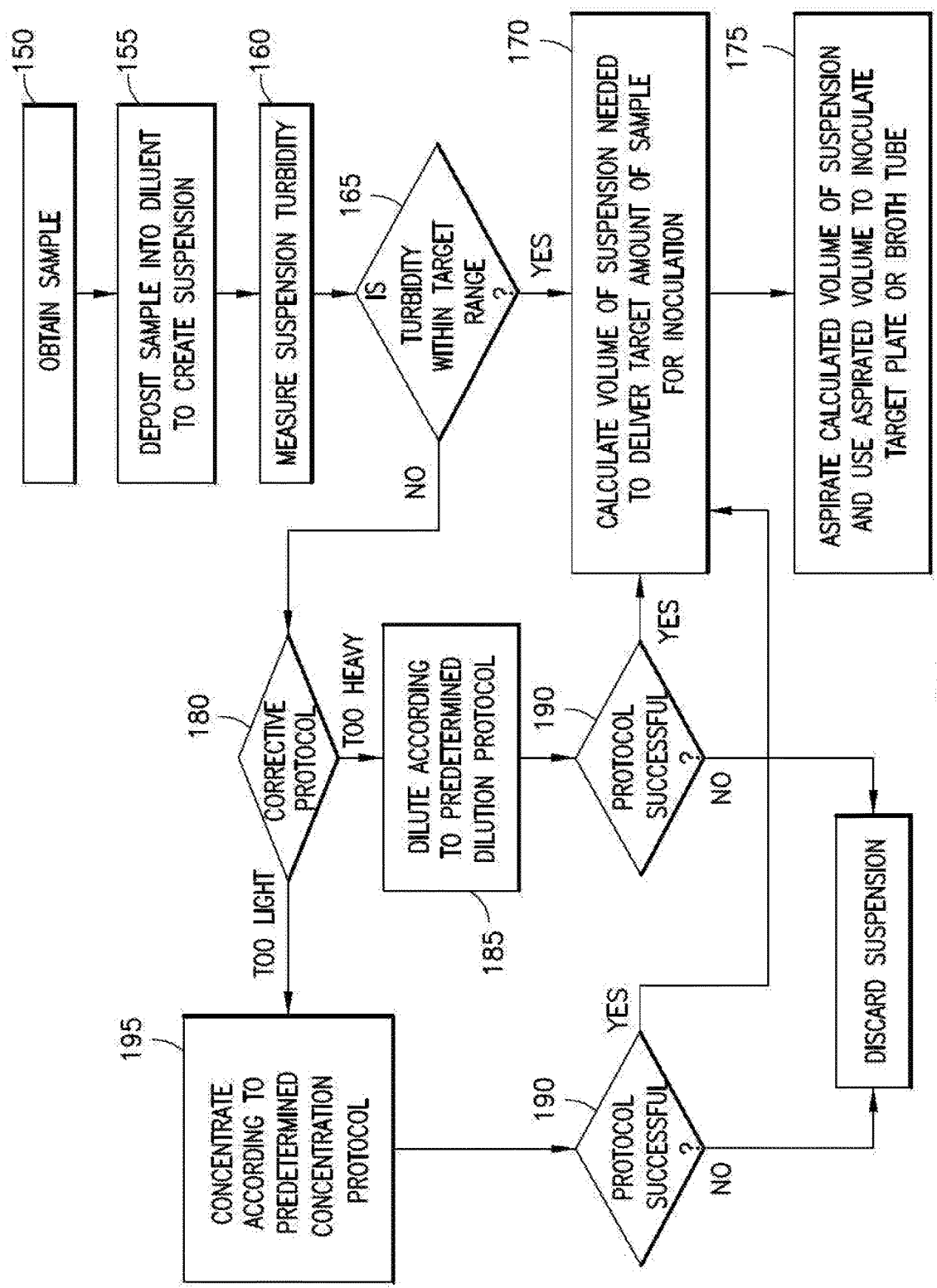
FIG. 1 is a flow chart that describes a method for using a suspension that does not require turbidity standardization prior to inoculation of a broth tube for AST.

Referring to FIG. 1, process begins with the step 150 of collecting sample (typically from a culture plate or culture tube) and, step 155, delivering that sample into a suspension. The turbidity of the suspension is measured at step 160 and the turbidity is then evaluated to determine if the measured turbidity is within a predetermined range at step 165. The predetermined range is necessary because the volume of sample that is used to inoculate the MALDI plate or broth tubes is limited by the volume that can be transferred by the automatic pipettor accurately and within the volume constraints of the pipettor. In this regard, current pipettors are configured to transfer no more than about 10 mL (i.e. 1000 µL) to about 12 mL (i.e. 1200 mL) of suspension.

If the suspension has a turbidity within the target range, then, based upon the turbidity reading, the required volume of suspension needed to inoculate the broth tube with the necessary amount of sample is calculated at step 170. The pipettor is used to aspirate the calculated volume of suspension from the suspension at step 175. If the suspension is too light, the volume required to inoculate the MALDI plate or broth tubes deliver the target amount of sample would be too large for the pipettor to accommodate (at least in one transfer). If the suspension is too heavy, then only a small volume of suspension is required for inoculation of the MALDI plate or broth tube. The aspiration and dispense of small volumes are difficult to precisely control, which makes it difficult to deliver the precise amount of sample for inoculation of the MALDI plate or broth tube. According to the method illustrated in FIG. 1, in one embodiment the predetermined turbidity is in the range of about 0.2 McFarland to about 2 McFarland. If the suspension is outside of this range, a corrective protocol is assigned at step 180. If the suspension is too concentrated, the suspension is subjected to a dilution protocol 185 that will reduce the concentration to the target range. The dilution protocol 185 is largely a matter of design choice and typically consists of removing some volume of suspension and replacing it with diluent. The volume of suspension removed is selected based on the turbidity measurement. If the dilution protocol 185 is successful, then, at step 190, the suspension is used to inoculate AST broth tubes by using the volume of suspension calculated in step 170. One illustrative example of a dilution protocol is described later herein. If the dilution protocol is not successful, the sample is discarded at step 191.

If at step 180 it is determined that the suspension is too dilute, the suspension is subjected to a concentration protocol at step 195 to increase the concentration of sample in the suspension. Such concentration protocols require the addition of sample into the suspension. The concentration protocol 195 is largely a matter of design choice and typically consists of adding some additional sample to the diluent. The amount of additional sample delivered into the suspension is difficult to control precisely, so a concentration protocol may require additional turbidity measurements to determine the turbidity of the suspension after the concentration protocol is completed. If the protocol is successful at step 190, then the suspension is used to inoculate a broth tube by calculating the volume of suspension required to inoculate the target amount of sample into the broth tube at step 170 and the volume of suspension is aspirated to inoculate the target plate at step 175. If the concentration protocol is not successful, then the sample is discarded at step 191.

One example of a dilution protocol is described later herein. Both the dilution protocol and the concentration protocol are contemplated to require an additional turbidity measurement after the suspension is concentrated or diluted.

The amount of the suspension that is used to inoculate plates for identification (e.g. MALDI plates) or broth tubes for antibiotic susceptibility testing (AST) is based on the amount of sample carried per unit volume of suspension. Once the suspension is created, if the concentration of the sample in suspension (i.e. sample turbidity) is too high (e.g. about 2 McFarland or above), then the volume of suspension required to inoculate that amount of sample onto the MALDI plate or into the AST broth tubes could be quite small. Small volumes are difficult to pipette accurately.

Consequently, if the amount of sample delivered into the suspension is such that the sample concentration in suspension (as measured by suspension turbidity) is higher than an upper threshold (e.g. above 2 McFarland) of a predetermined range then the suspension is subjected to a dilution protocol to reduce the turbidity such that suspension turbidity is within the predetermined range. If the amount of sample delivered into suspension is such that the suspension turbidity is below the lower threshold (e.g. below about 0.2 McFarland) of the predetermined range, then additional sample is acquired to increase the concentration of the sample in the suspension (if no additional sample is available, then the suspension is set aside).

In one example, the measured turbidity of the prepared suspension is in the range of about 3 McFarland. In this example, the predetermined turbidity range is about 0.2 McFarland to about 2 McFarland. Based on this turbidity measurement, the system determines to subject this suspension to a dilution protocol.

The predetermined turbidity range is largely a matter of design choice. Factors that determine the broad range include: i) the accuracy of the apparatus used to measure turbidity (e.g. the nephelometer); ii) the reading window of the nephelometer; and iii) the accuracy and capacity of the pipettor. According to the method the suspension is created with a high higher McFarland value and then diluted to reduce the turbidity to a value that will deliver a target amount of sample to ID or AST test.

In another example, sample is obtained and inoculated into a suspension diluent. The turbidity of the suspension is measured. The measured turbidity is determined to be within the predetermined range (e.g. about 0.2 McFarland to about 2 McFarland). Based on the amount of sample required for inoculation, a volume of suspension is obtained that will carry the target amount of sample onto the MALDI plate or into the AST broth tube. According to one embodiment, the suspension is prepared by picking an amount of a colony from a culture dish and delivering the picked sample into the suspension.

In another example, the sample is obtained and inoculated into the suspension diluent. The measured turbidity is determined to be below the predetermined range (i.e. below about 0.2 McFarland). In this example, additional sample is acquired and inoculated into the suspension to increase the sample turbidity. The turbidity of the suspension is remeasured. If the turbidity is within the predetermined range, a specified volume of the suspension is obtained to deliver the target amount of sample onto the MALDI plate or into the AST broth tube. If the adjusted turbidity is too high, then a dilution protocol is used to dilute the suspension. If the adjusted turbidity remains too low, the process is repeated (if there is additional sample remaining to be acquired). If there is no additional sample, then the suspension is not used and is set aside from the automated process. If repeated attempts are made to obtain a suspension with a turbidity within the predetermined range are unsuccessful, then the suspension is set aside from the automated process.

The volume of suspension diluent is largely a matter of design choice. The volume of suspension cannot be too low, as this will cause the turbidity of the suspension to be much higher than the target turbidity range, requiring multiple dilution steps to obtain a suspension with the target turbidity. The volume of the suspension volume cannot be too high, or the turbidity of inoculated suspensions will be too low, requiring multiple steps to acquire a suspension concentration within the target turbidity range.

In one embodiment, the volume of the suspension diluent into which the sample is initially inoculated is about 200 µL to about 400 µL. Alternatively, the range of suspension diluent volume is about 250 µL to about 350 µL. In one example, the volume of the suspension diluent into which the sample is inoculated is about 300 µL.

Figure 2:
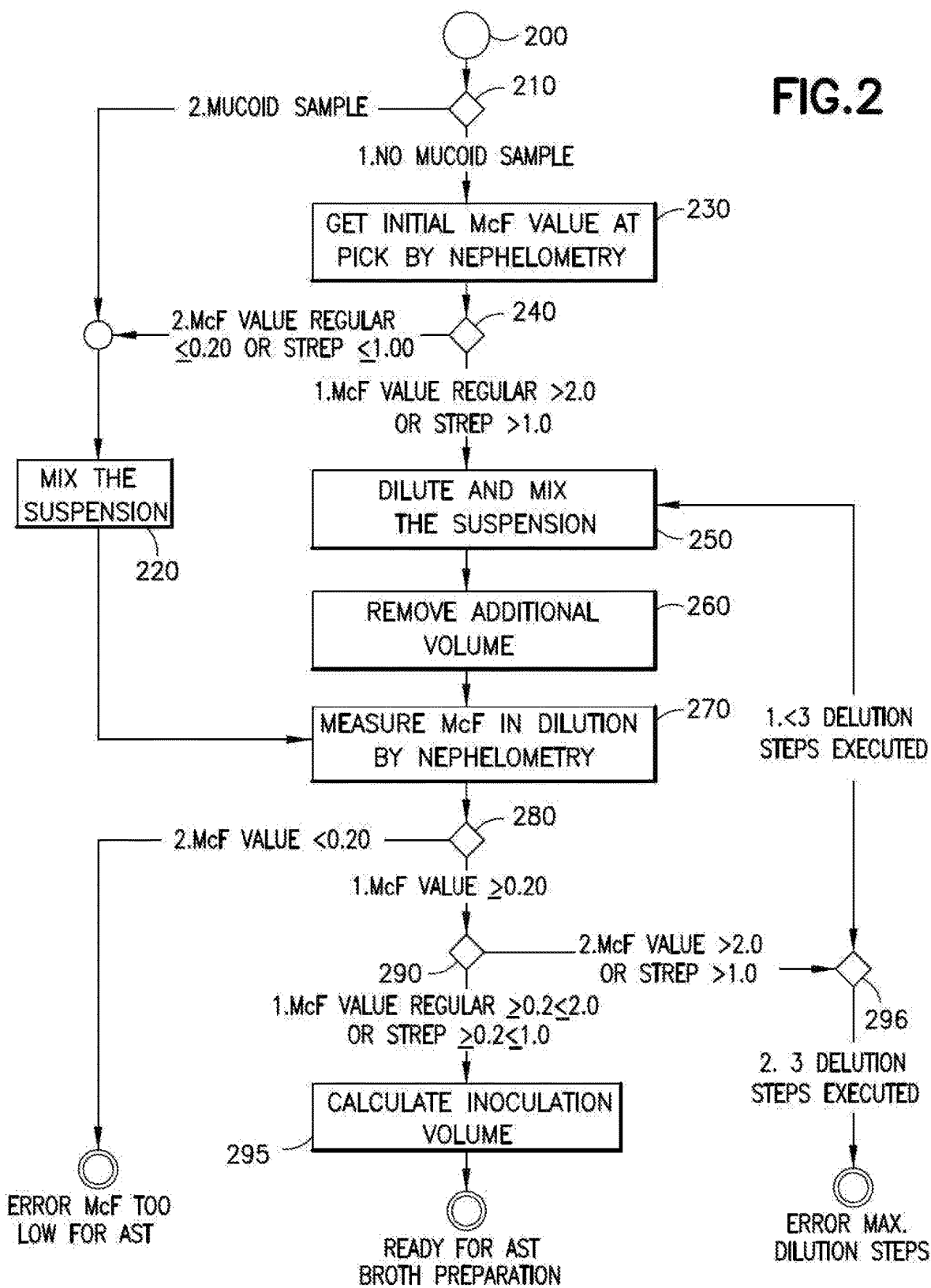
FIG. 2 is a flow chart that describes a method for using a suspension that does not require turbidity standardization prior to inoculation of a broth tube for AST but does provide a dilution protocol for preparing a sample suspension when the initial suspension is too concentrated.
Figures 3, 3A, 3B:
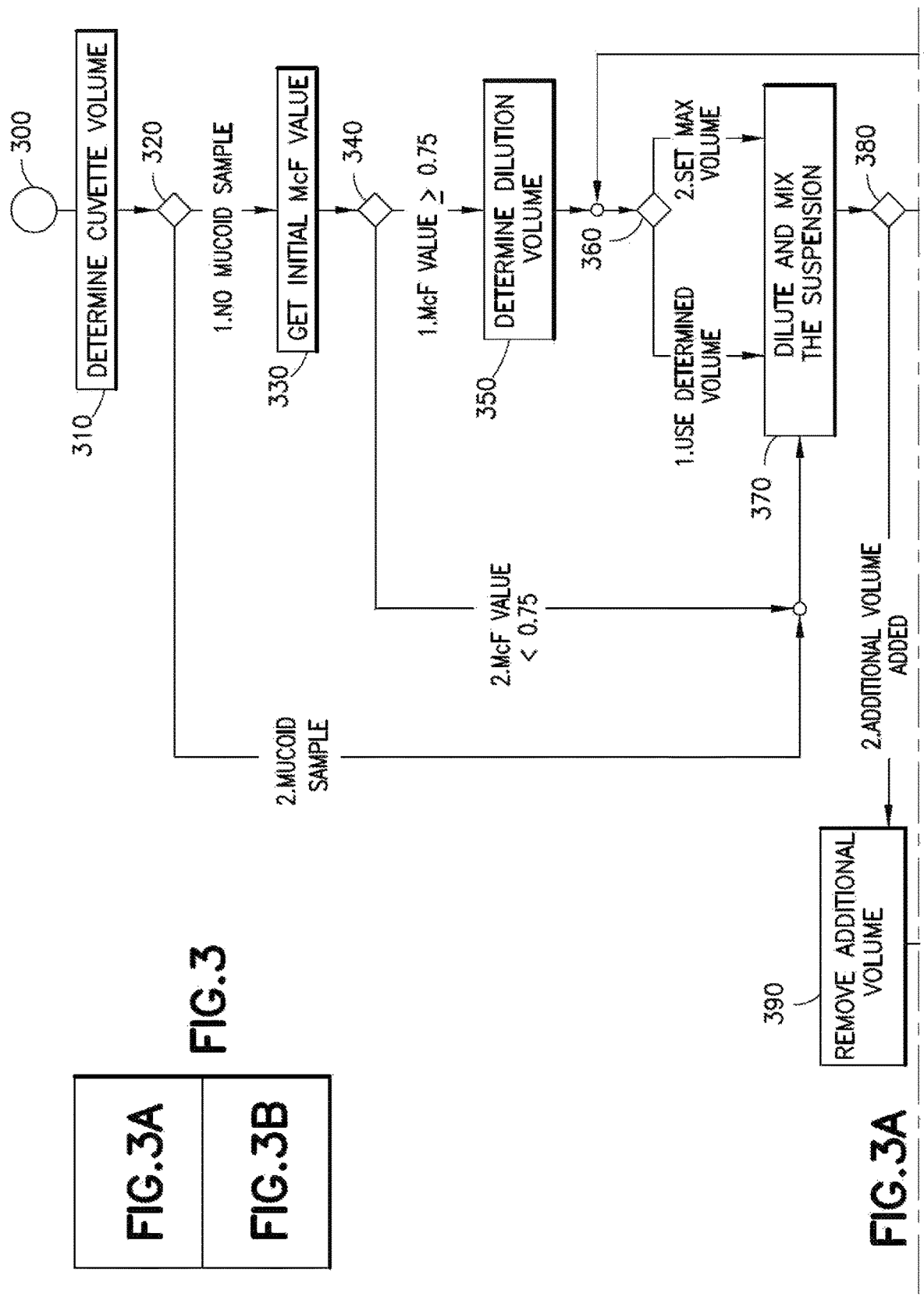
FIG. 3 is a flow chart that describes a method for using a suspension that does not require turbidity standardization prior to inoculation of a broth tube for AST but does provide a dilution protocol for preparing a sample suspension according to another embodiment of the invention that is divided into FIG. 3A and FIG. 3B.
FIG. 3A illustrates the first part of the method and FIG. 3B describes the second part of the method.
Figure 3B:
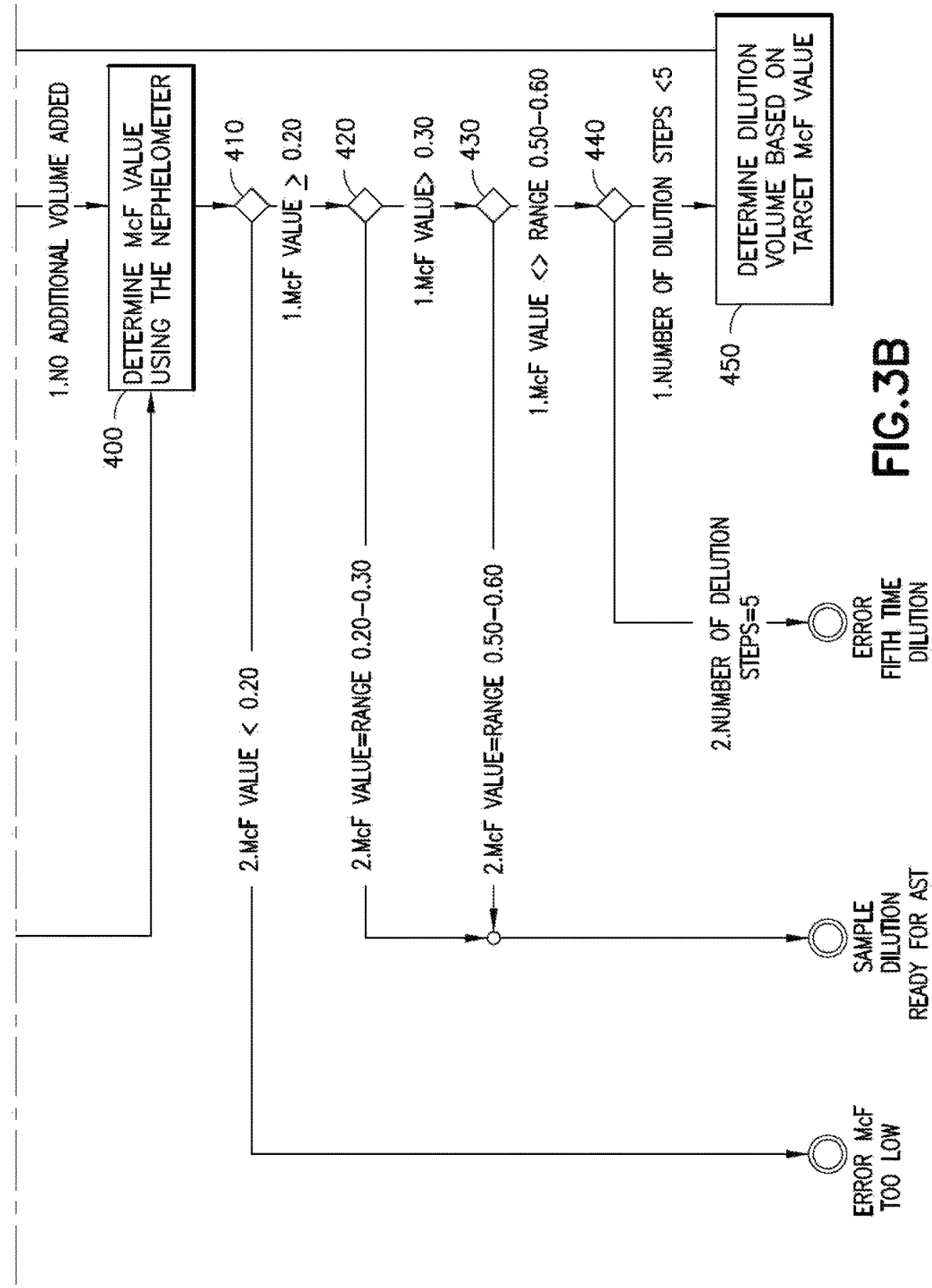

Examples of workflows with specific concentration/dilution protocols are illustrated in FIGS. 2 and 3. In general, the sample is acquired at step 200. At 210, if the sample is determined to be a mucoid sample, then the sample is mixed with diluent at step 220 and its turbidity (in McFarland) is measured at step 270.

If the sample is not a mucoid sample then the turbidity of the sample is determined prior to dilution at step 230. At step 240, if the initial McFarland value of the suspension for a regular sample is greater than 2 McFarland, or if the initial McFarland value of the suspension for a sample suspected to contain Streptococcus is greater than about 1 McFarland, the suspension proceeds to step 250 where deionized water is added to the suspension and the suspension is mixed. If the initial McFarland value for the regular sample is less than or equal to about 2 (or for a sample suspected to contain Streptococcus, if the initial McFarland value is less than or equal to 1) the sample is ready to be mixed and the sample proceeds to step 220.

At step 250, in an automated system with a robotic pipettor, the robotic pipettor picks up a 1000 µL pipette tip and dispenses 950 µl of deionized water into the cuvette containing the suspension. If the sample is suspected to contain Streptococcus then the robotic pipettor picks up a 1000 µL pipette tip and dispenses 495 µl of deionized water into the cuvette containing the suspension. In a manual procedure the 1000 µL pipette tip is obtained and the amount of deionized water described above is dispensed into the suspension.

At step 220, a 1000 µL aliquot of the suspension is obtained and is used to mix the sample by a series of about five (5) aspirations and dispenses of about 250 µL of the suspension. The pipette tip is then discarded.

At step 260, the deionized water that was not dispensed into the suspension in step 250 is dispensed into waste. Also, if the volume of the diluted sample exceeds the volume upper limit, the excess volume of the suspension is removed.

At step 270, the turbidity of the diluted suspension is measured using a nephelometer. Measuring turbidity and devices used for measuring turbidity are well known to those of skill in the art and are not described in detail herein. Methods and apparatus for measuring turbidity are described in WO 2016/034554. In the FIGS. 2 and 3 protocols, any step that causes a change in the concentration of the sample in the suspension requires a new turbidity measurement since the sample turbidity value determines how the suspension is processed in the workflow illustrated in FIGS. 2 and 3.

At step 280, the measured sample turbidity is evaluated. If the McFarland value of the cuvette suspension is less than 0.2 then the suspension cannot be used to inoculate the AST broth tubes. The system will link the sample with an error flag to ensure that the suspension is not used to inoculate the AST broth tubes. The system is updated with this information and the suspension is set aside. If the McFarland value for the suspension is greater than 0.2, then the suspension can potentially be used to inoculate the AST broth tubes.

At step 290, if the McFarland value for the suspension is greater than or equal to 0.2 but less than or equal to 2 (if the sample is suspected to contain *Streptococcus* then that range is greater than or equal to 0.2 but less than or equal to 1) then the method proceeds to step 295 where the inoculation volume of the suspension that will deliver the target amount of sample into the AST broth tubes is calculated.

The volume is calculated for regular AST broths using the following relationship:

$$\text{Added Volume} = (0.55 \div (\text{measured McFarland value for the suspension})) \times 47.5 \ \mu L \quad (1)$$

For example, if the measured turbidity for the suspension is 2.3 then the volume of the suspension used to inoculate the AST broth tube is $(0.55 \div 2.3) \times 47.5 \ \mu L = 11.36 \ \mu L$. If the sample is a *Streptococcus* AST sample, then the broth is inoculated with a volume according to the following relationship:

$$\text{Added volume} = (0.55 \div (\text{measured McFarland value for the suspension})) \times 25.00 \ \mu L \quad (2)$$

If the McFarland value is greater than 2 (1 if the suspension is suspected to contain *Streptococcus*) then at step 296 the number of times that the sample has been diluted is determined. If the number of dilutions is less than three, the suspension is returned to step 250 for further dilution and mixing (and suspension volume reduction if required for further dilution). If the number of dilutions is three (3) then an error message issues as the sample has exceeded the maximum number of dilution steps permitted.

FIG. 3 describes a process by which a suspension is used to inoculate a broth tube without standardizing the turbidity of the suspension. The process begins with a prepared suspension from which a small amount has been removed and used to inoculate a MALDI plate. Referring to FIG. 3A, that suspension is obtained at step 300. At step 310, the volume of the suspension after MALDI spotting is determined. The actual volume is determined according to the following relationship:

$$\text{Actual volume} = V_s \text{ (e.g. 330 } \mu L) - ((\text{number of target plate spots} \times \text{number of suspension layers}) \times V_{spot} \text{ [e.g. 3 } \mu L]) - (\text{number of layers} \times \text{buffer margin}) - (\text{evaporation rate} \times \text{deck life in hours}) \quad (3)$$

In the above equation, $V_s$ is the suspension volume, $V_{spot}$ is the per spot volume of suspension deposited on the MALDI plate. For example, a cuvette containing a suspension from which sufficient volume for one spot and 4 layers on a target plate has been removed would have a volume of 330 $\mu L - ((1 \times 4) \times 3 \ \mu L) - (4 \times 3) - (10 \times 3) = 276 \ \mu L$ of actual cuvette suspension volume. This assumes that the suspension has a deck life of three hours. At step 320, the sample is evaluated to determine if it is a mucoid sample or not. If the sample is mucoid, then the sample proceeds to step 370, where the sample is diluted and the suspension is mixed and its turbidity measured. If the sample is not mucoid, the sample proceeds to step 330. The initial turbidity determination of the suspension is used to start the processing of the initially heavy suspension so that the suspension can be used to inoculate a broth tube for AST.

At step 340, if the initial turbidity of the suspension is greater than or equal to a predetermined threshold (e.g. 0.75 McFarland), then deionized water is added to the suspension and the suspension is mixed in step 350. If the initial turbidity of the suspension is less than the predetermined threshold (e.g., 0.75 McFarland), then the method proceeds to step 370 for that suspension. As mentioned elsewhere herein, the turbidity and volume thresholds set forth in the descriptions of FIGS. 2 and 3 are by way of example and not by limitation.

At step 350, a pipette tip (1000 $\mu L$) is obtained and dispenses a volume of deionized water into the target cuvette. This can be done manually or using a robotic pipettor mounted on a gantry. The volume of deionized water that is dispensed is calculated by the following formula:

$$\text{Volume of deionized water} = ((\text{Initial McFarland value} \div 0.75) \times \text{actual cuvette volume}) - \text{actual cuvette volume} \quad (4)$$

According to equation 4, the ratio of the actual McFarland value to the threshold McFarland value is used to determine the volume of deionized water added. If the actual McFarland value is below the upper threshold, no deionized water is added to the suspension. Using the example above with an initial McFarland value of 1.4 the volume of deionized water is $((1.4 \div 0.75) \times 276 \ \mu L) - 276 \ \mu L = 239 \ \mu L$. At step 360, if the calculated volume is less than the maximum volume (e.g. 950 $\mu L$ for a 1000 $\mu L$ pipette tip), then the calculated volume of deionized water is added to the sample (indicated as "use determined volume" in FIG. 3A). If the amount of deionized water to be added exceeds 950 $\mu L$, then only the maximum volume of 950 $\mu L$ is added (indicated as "set max volume" in FIG. 3A).

At step 370, a pipette tip (1000 $\mu L$) is used to mix the sample by a series of about five (5) aspirations and dispenses of about 250 $\mu L$ of the suspension. After the fifth cycle the pipette tip is then discarded.

At step 380 it is determined if additional volume (i.e. deionized water) needs to be added to the suspension. If additional volume is required, the suspension proceeds to step 390, where additional diluent (deionized water) is added to the suspension. If the added volume causes the suspension to exceed volume limitations, then suspension is removed to reduce the suspension volume so that the volume is at or below the upper volume limit. If no additional diluent is needed, the method proceeds to step 400 (FIG. 3B), where a nephelometer is used to measure the turbidity of the suspension. Subsequent processing of the suspension is determined by the measured turbidity (in this embodiment, the measured turbidity is measured in McFarland).

Specifically, if the McFarland value is less than 0.2, the suspension cannot be used and an error message results. See step 410 in FIG. 3B. If the McFarland value is greater than or equal to 0.2, then, at step 420, if the McFarland value is 0.2 to 0.3 (this is a 0.25 McFarland value+/−20 percent), the suspension is used as a source for sample for the AST panel.

If the McFarland value is greater than 0.3 then, at step 430, it is determined if the McFarland value is in the range of 0.5 to 0.6 (this is a 0.55 McFarland value+/−10 percent). Such suspensions are determined to be suited for use as a source for sample for inoculating a broth for use in an AST panel. If the turbidity of the suspension is outside the range of 0.5 to 0.6 McFarland at step 430, then the sample proceeds to step 440 where the number of prior dilutions of the suspension determines the further processing of the suspension. If the suspension has been diluted 5 times, then an error message issues for that suspension and it is not used as a source for sample for AST broth inoculation.

If the suspension has been diluted less than five times, then, at step 450, the suspension returns to step 360 for further dilution at step 370. For those suspensions determined to have McFarland values in the predetermined range that makes such suspensions suitable for use as a source for sample for AST broth inoculation, the suspensions are diluted without further turbidity measurements according to the following schedule in Table 1.

TABLE 1

| McFarland value in range | Target McFarland value |
|---|---|
| 0.31 to 0.49 | 0.25 |
| 0.61 to 0.99 | 0.55 |
| ≥1.00 | 0.75 |

To obtain a suspension with the target McFarland volume from samples having turbidity in the ranges described in Table 1 above, the sample is diluted according the following relationship:

Added volume=((measured McFarland value (step 370)÷target McFarland value)×actual volume)−actual volume (5)

For example, using the cuvette volume at step 350, if the initial measured McFarland value of the suspension is 1, then the added volume equals ((1−0.75)×276)−276 which is 92 μL of diluent (e.g. deionized water) to be added to the suspension to yield a suspension with a target McFarland value of 0.75. However, if the amount of volume to be added exceeds 950 μL, only 950 μL is added to the sample.

At step 370, once the added volume is determined, the specified volume of diluent (e.g. deionized water) is added to the sample. A 1000 μL pipette tip is obtained for this purpose (in automated environments, a robotic pipettor acquires a pipette tip and the pipettor is then translated via a gantry to position the pipettor over the suspension). The pipette tip is used to mix the suspension by aspirating a volume of suspension and then dispensing the volume of suspension from the pipette tip. The last fifty (e.g., 50 μL) is dispensed with the pipette tip above the suspension to ensure that the pipette tip is completely empty.

If the target McFarland value is 0.55 or 0.25 and the total volume of the suspension in the cuvette is greater than 1500 μL after dilution, then volume is removed from the suspension so that the suspension does not exceed the maximum volume. Referring to step 390, the excess volume is removed according to the following formula:

Volume to be removed=actual volume (μL)−1500 μL (6)

However, if the number of dilutions exceeds 5, then the sample has been diluted too often and cannot be used for automated AST follow up. In such instances an error message will result. If the number of prior dilutions is less than five then the suspension is returned to step 360 for dilution as previously described.

The above method in which the volume of the AST inoculum was calculated according the above methods (instead of adjusting the McFarland value of the heavy suspension created for MALDI and inoculating the AST panels with a predetermined volume based on a turbidity (e.g. McFarland) specification)) was evaluated to determine its efficacy for AST broth inoculation. For this determination the *E. coli* QC strain, BACTEC A25922, was used to test the reproducibility of calculating the volume of inoculum needed to achieve an acceptable concentration of organism in the AST broth tube. The predetermined range of concentration is between $2 \times 10^5$ and $8 \times 10^5$ CFU/mL for *E. coli* (BACTEC A25922). BACTEC A25922 was also used to compare the method describe herein (wherein the suspension is evaluated and a volume of suspension is determined based on the suspension turbidity) to a process in which a heavy suspension is prepared for MALDI which is then diluted to a target turbidity (e.g. either 0.5-0.6 McFarland or 0.2-0.3 McFarland and a consistent volume of that suspension is used to inoculate the AST broth tube. Twenty (20) samples were tested using both methods (40 samples in total), and plate counts were used to measure the bacterial concentration in the AST broth tube. The AST results from the processed AST panels were also analyzed.

As reported in FIG. 6, all 40 samples resulted in AST broth concentrations within $2 \times 10^5$ to $8 \times 10^5$ CFU/mL for a variety of starting McFarland values. All of the minimum inhibitory concentrations were in exact agreement for all 40 samples. Therefore, it was concluded that the process for diluting a heavy suspension and then determining the volume of the suspension required to deliver a target amount of sample into the AST broth is reproducible and performs equally to a dilution process to a standardized turbidity value (McFarland) for this QC strain.

Figure 4:
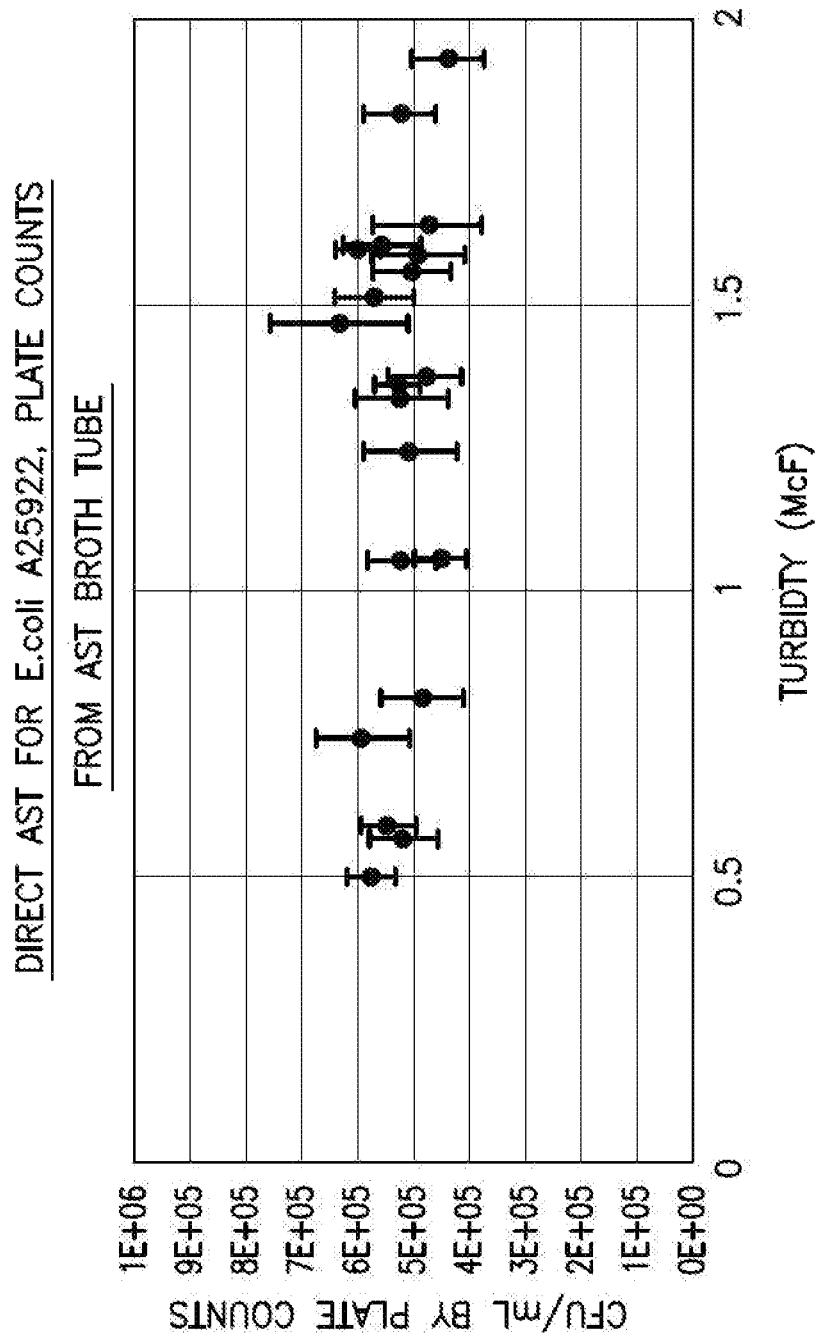
FIG. 4 illustrates *E. coli* concentration in the AST broth tube versus the final turbidity of the suspension using the method illustrated in FIG. 2.

Referring to FIG. 4, the *E. coli* concentration in the AST broth tube versus the final turbidity of the suspension used to inoculate the AST broth tube using Direct AST is illustrated. The error bars represent the standard deviation of the 9 plate counts prepared for each sample. The top and bottom dashed lines indicate the limits of the acceptable concentration range, $2 \times 10^5$ to $8 \times 10^5$ CFU/mL, and the dashed line in the middle represents the middle of the range ($5 \times 10^5$ CFU/mL).

Figure 5:
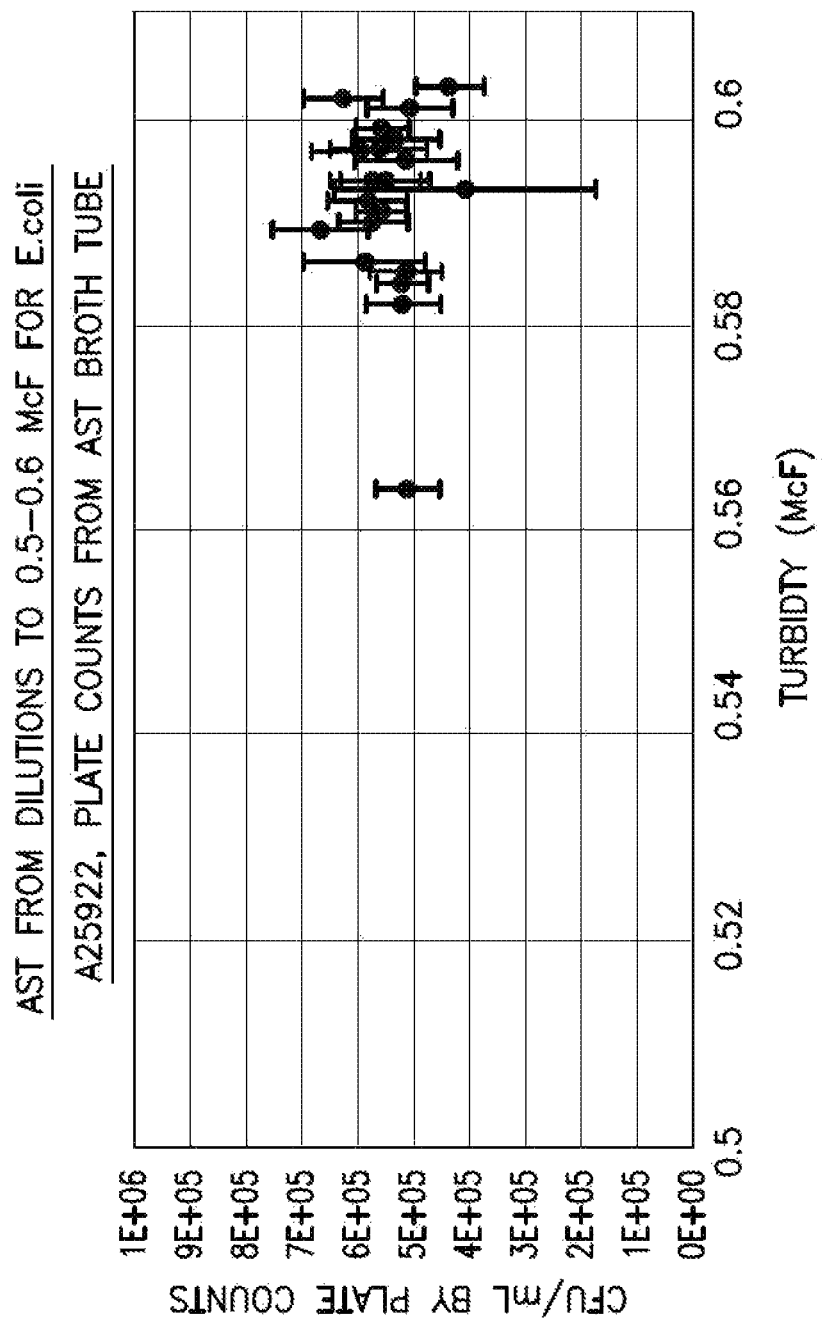
FIG. 5 illustrates *E. coli* concentration in the AST broth tube versus the final turbidity of the suspension using the method illustrated in FIG. 2 for a suspension created using only one turbidity measurement.

Referring to FIG. 5, the *E. coli* concentration in the AST broth tube versus the final turbidity of the suspension used to inoculate the AST broth tube using a dilution scheme to dilute the suspension to a target McFarland value (0.5-0.6 McFarland). The error bars represent the standard deviation of the 9 plate counts prepared for each sample. The top and bottom dashed lines indicate the limits of the acceptable concentration range, $2 \times 10^5$ to $8 \times 10^5$ CFU/mL, and the dashed line in the middle represents the middle of the range ($5 \times 10^5$ CFU/mL).

Referring to FIG. 6, the minimum inhibitory concentration (MIC) for each antibiotic was the same, whether the turbidity of the suspension was adjusted to be within a target turbidity or whether the volume of the inoculum was adjusted to inoculate a target amount of sample into the AST broth.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for preparing a sample suspension to provide a target amount of sample comprising:
 inoculating a sample suspension container with a biological sample into a sample diluent to form a biological sample suspension, wherein the biological sample is suspected to contain one or more microorganisms;

determining whether the biological sample is suspected to contain a mucoid or non-mucoid sample;

if the biological sample is a non-mucoid sample, measuring a turbidity of the biological-sample suspension containing the non-mucoid sample for a first time;

if the biological sample is a mucoid sample, mixing the mucoid sample with sample diluent to form a mucoid biological sample suspension then measuring the turbidity of the mucoid biological sample suspension for a first time;

determining if the measured turbidity of the biological sample suspension or the mucoid biological sample suspension is within a predetermined range;

calculating a volume of the biological sample suspension or the mucoid biological sample suspension that is required to inoculate a culture medium based on a ratio of a predetermined target turbidity for a biological sample suspension or a mucoid biological sample suspension for culture medium inoculation and the measured turbidity multiplied by a volume of the biological sample suspension or the mucoid biological sample suspension required to deliver a predetermined amount of biological sample into the culture medium; and depositing the calculated volume of the biological sample suspension or the mucoid biological sample suspension onto the culture medium.

2. The method of claim 1, further comprising:

if the measured turbidity of the biological sample suspension or the mucoid biological sample suspension is below the predetermined range, performing a concentration protocol to increase the turbidity of the biological sample suspension or mucoid biological sample suspension and re-measuring the turbidity of the biological sample suspension or mucoid biological sample suspension; and if the measured turbidity of the biological sample suspension or the mucoid biological sample suspension is above the predetermined range, performing a dilution protocol to decrease the turbidity of the biological sample suspension or the mucoid biological sample suspension and re-measuring the turbidity of the biological-sample suspension or the mucoid biological sample suspension.

3. The method of claim 2, wherein the concentration protocol comprises adding additional sample to the biological sample suspension or the mucoid biological sample suspension prior to re-measuring the turbidity of the biological sample suspension or the mucoid biological sample suspension.

4. The method of claim 2, wherein the dilution protocol comprises adding additional diluent to the biological sample suspension or the mucoid biological sample suspension prior to re-measuring the turbidity of the biological sample suspension or the mucoid biological sample suspension.

5. The method of claim 3, wherein the concentration protocol further comprises:

determining if the biological sample suspension or the mucoid biological sample suspension is above a pre-determined volume specification; and removing an excess volume of the biological sample suspension or the mucoid biological sample suspension from the sample suspension container to provide the biological sample suspension or the mucoid biological sample suspension within the predetermined volume specification prior to adding the additional sample to the biological sample suspension or the mucoid biological sample suspension.

6. The method of claim 4, wherein the dilution protocol further comprises:

determining if the biological sample suspension or the mucoid biological sample suspension is above a pre-determined volume specification; and removing an excess volume of the biological sample suspension or the mucoid biological sample suspension from the sample suspension container to provide the biological sample suspension or the mucoid biological sample suspension within the predetermined volume specification prior to adding the additional diluent to the biological sample suspension or the mucoid biological sample suspension.

7. The method of claim 5, wherein, if the re-measured turbidity of the biological sample suspension or the measured turbidity of the mucoid biological sample suspension is within a pre-determined range of turbidity values, calculating the volume of the biological sample suspension or the mucoid biological sample suspension required to inoculate a culture medium based on a ratio of a predetermined target turbidity for a sample suspension for culture medium inoculation and multiplied by a volume of the biological sample suspension or the mucoid biological sample suspension required to deliver the predetermined amount of biological sample into the culture medium using the biological sample suspension or the mucoid biological sample suspension having the predetermined target turbidity; and depositing the calculated volume of the biological-sample suspension or the mucoid biological sample suspension onto the culture medium.

8. The method of claim 6, wherein, if the re-measured turbidity of the biological sample suspension or the measured turbidity of the mucoid biological sample suspension is within a pre-determined range of turbidity values, calculating the volume of the biological sample suspension or the mucoid biological sample suspension required to inoculate a culture medium based on a ratio of a predetermined target turbidity for a sample suspension for culture medium inoculation and the re-measured turbidity of the biological sample suspension or the measured turbidity of the mucoid biological sample multiplied by a volume of the biological sample suspension or the mucoid biological sample suspension at the predetermined target turbidity required to deliver the predetermined amount of biological sample into the culture medium; and depositing the calculated volume of the sample suspension onto the culture medium.

9. The method of claim 5, wherein, if the re-measured turbidity is not within a pre-determined range of turbidity values, repeating the concentration protocol.

10. The method of claim 6, wherein, if the re-measured turbidity is not within a pre-determined range of turbidity values, repeating the dilution protocol.

11. The method of claim 9, further comprising discarding the biological-sample suspension or the mucoid biological sample suspension or sample if the concentration protocol has been repeated a predetermined number of times.

12. The method of claim 10, further comprising discarding the biological sample suspension or the mucoid biological sample suspension, if the dilution protocol has been repeated a predetermined number of times.

13. The method of claim 1, wherein the biological sample suspension comprises *Streptococcus*.

* * * * *